United States Patent [19]

Fischer, Jr. et al.

[11] 4,394,527

[45] Jul. 19, 1983

[54] METHOD FOR THE LIQUID PHASE OXIDATIVE FLUORINATION OF AROMATIC COMPOUNDS

[75] Inventors: Robert G. Fischer, Jr., Fairfield; Arnold Zweig, Westport, both of Conn.

[73] Assignee: American Cyanamid Company, Stamford, Conn.

[21] Appl. No.: 87,135

[22] Filed: Oct. 22, 1979

[51] Int. Cl.³ .............................................. C07C 17/12
[52] U.S. Cl. .................................................. 570/143
[58] Field of Search ........................ 260/650 F, 649 F; 570/143

[56] References Cited

U.S. PATENT DOCUMENTS 2,759,026  8/1956  McCleary ........................ 260/650 F
2,993,937  7/1961  Pavlath ............................ 260/650 F Primary Examiner—Charles F. Warren
Assistant Examiner—Joseph A. Boska
Attorney, Agent, or Firm—H. G. Jackson

[57] ABSTRACT

There is provided a process for effecting fluorination of benzene, p-difluorobenzene or p-dichlorobenzene by subjecting the same to the action of argentic fluoride ($AgF_2$) in the liquid phase to obtain fluorobenzene from benzene or a fluorinated cyclohexadiene from halogenated benzene, respectively, in good yield and purity.

4 Claims, No Drawings

METHOD FOR THE LIQUID PHASE OXIDATIVE FLUORINATION OF AROMATIC COMPOUNDS

The present invention relates to the fluorination of benzene, p-difluorobenzene or p-dichlorobenzene in the liquid phase. More particularly, it relates to the fluorination of benzene or p-difluorobenzene in an inert solvent comprising subjecting the latter mixture to the action of argentic fluoride and recovering desired product in good yield and purity.

As is known, aromatic compounds and, particularly benzene, have been subjected to fluorination. One such method involves the reaction of aniline and sodium nitrite in the presence of hydrogen fluoride to obtain monofluorobenzene. However, because of the formation of metastable diazonium salt intermediate, the overall process becomes expensive due to the costly handling of the diazonium salt. Another method involves the use of a mixture of xenon fluoride, benzene and hydrogen fluoride. Nonetheless, there is actual loss and non-recoverability of very expensive xenon. Still another method which has proven itself not entirely satisfactory is the use of elemental fluorine. Such direct fluorination of benzene is highly dangerous, requiring extremely low temperatures and nearly infinite fluorine dilution. If a process could be provided so that monofluorobenzene or fluorinated cyclohexadiene can be directly obtained in an economical and safe manner and in good yield, such process would fulfill a long felt need in the art.

To this end, there is provided a straightforward and safe process for obtaining monofluorobenzene in good yield and purity. Benzene or other suitable aromatic compound, such as p-difluorobenzene or p-dichlorobenzene, is diluted with an inert solvent and admixed with argentic fluoride at a temperature between about 25° C. and 100° C. A good yield of monofluorobenzene is obtained when benzene is treated and 3,3,6,6-tetrafluoro-1,4-cyclohexadiene results when p-difluorobenzene or p-dichlorobenzene is employed.

According to the process of the invention, an aromatic compound, such as benzene, p-difluorobenzene or p-dichlorobenzene is admixed with an inert solvent to which is then added argentic fluoride to recover the respective fluorinated aromatic compound. Resultant compound which is obtained in the liquid phase is recovered in good yield and purity.

Illustrative of the inert organic solvents employed herein are: a linear or cyclic aliphatic hydrocarbon of from 5 to 18 carbon atoms, or higher, such as hexane, dodecane, as well as halogenated solvents, such as chloroform or carbon tetrachloride, hexane being a preferred solvent. Usually, an amount ranging from about 99% to about 50% of solvent and from about 1% to about 50% of the hereinabove defined aromatic compound are employed.

To the latter solvent mixture is added from about 0.1 mol to about 1.0 mol of argentic fluoride per mol of benzene and held preferably under a nitrogen atmosphere at a temperature between about room temperature, namely 25° C., and 100° C. and, preferably, at reflux temperatures.

Subsequent to reaction wherein the argentic fluoride is converted from a reddish brown coloration to the bright yellow of argentous fluoride, there is recovered monofluorobenzene useful in pesticide synthesis and a cyclohexadiene useful as a monomer in synthetic rubber synthesis. Since argentous fluoride is insoluble in the organic layer, the overall mixture is subject to filtration and the recovered argentous fluoride can be revivified to argentic fluoride by any method known in the art as by fluorinating the same with fluorine.

Yields of desired product in the range of from about 25% and higher result from the practice of the present invention.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE I

Preparation of monofluorobenzene

In a 250 ml teflon Erlemeyer flask containing a teflon coated magnetic stirring bar and fitted with a teflon condenser is placed 30 ml of n-hexane and 20 ml (0.23 moles) of benzene. The flask is flushed with nitrogen for one hour and 10 g (0.068 mole) of argentic fluoride ($AgF_2$) is added all at once. The mixture is stirred at room temperature for 15 minutes, then brought to reflux using a heated oil bath and allowed to reflux for 18 hours. The mixture is allowed to cool to room temperature under nitrogen. The resulting organic layer which is a slurry, is pale yellow and the color of the precipitate therein has changed from the dark red-brown of $AgF_2$ to the bright yellow of argentous fluoride (AgF). The slurry is next filtered and the organic layer washed with water. The organic layer is dried over sodium sulfate and analyzed by $^{19}F$ NMR. Analysis indicates a 61% yield of fluorobenzene based on the complete consumption of the $AgF_2$ reagent.

EXAMPLE II

Preparation of Monofluorobenzene

The procedure of Example I above is repeated using 60 ml of n-hexane and 40 ml of benzene with 10.0 g $AgF_2$. The reaction conditions are identical to those of Example I above. Analysis as described in Example I indicates a 61% yield of fluorobenzene.

EXAMPLE III

Preparation of Monofluorobenzene

The procedure of Example I is repeated using 30 ml of methylene chloride solvent in place of n-hexane, 17 ml (0.068 mols) of benzene, and 10.0 g (0.068 mols) of $AgF_2$. The reaction mixture was stirred and held at 25° C. for 18 hrs. Analysis as described in Example I indicates a 44% yield of fluorobenzene.

EXAMPLES IV-IX

The procedure of Example I is repeated employing a plurality of solvents, concentrations and proportions of of benzene and $AgF_2$ reactants, reaction times and temperatures. The condition and yield of fluorobenzene as determined by the method described in Example I are reported in Table I below. In each of the examples, 10.0 g (0.068 moles) $AgF_2$ is employed.

TABLE I

| Ex. No. | Solvent | Solvent Volume (ml) | Benzene (moles) | Benzene (Vol. %) | T °C. | Time Hrs. | PhF |
|---|---|---|---|---|---|---|---|
| IV | $CHCl_3$ | 10 | .068 | 38 | 62 | 18 | 28 |
| V | $CCl_4$ | 25 | .068 | 20 | 76 | 18 | 36 |
| VI | n-hexane | 30 | .068 | 17 | 69 | 18 | 50 |
| VII | n-hexane | 50 | .068 | 11 | 69 | 18 | 48 |
| VIII | n-hexane | 30 | 0.67 | 67 | 69 | 0.2 | 45 |
| IX | n-hexane | 9.1 | .068 | 40 | 40 | 0.2 | 47 |

EXAMPLE X

Preparation of 3,3,6,6-Tetrafluoro-1,4-cyclohexadiene

Using the apparatus and procedures described in Example I above, 7.75 g. (0.068 moles) of p-difluorobenzene in 30 ml of n-hexane is reacted with 10.0 g (0.068 moles) of $AgF_2$ at reflux (about 69° C.) for 10 minutes. Analyses of the product by the method of Example I indicated an 82% yield of 3,3,6,6-tetrafluoro-1,4-cyclohexadiene, based on complete consumption of the $AgF_2$ reactant. The analysis also indicated 58% of the initial charge of p-difluorobenzene had not reacted.

In lieu of p-difluorobenzene used in Example X above, p-dichlorobenzene can also be employed to yield tetrafluoro-1,4-cyclohexadiene in reduced yields of less than 82%, based on argentic fluoride charge.

We claim:

1. A process for monofluorinating a benzene nucleus which comprises: reacting at a temperature ranging from about 25° C. to about 100° C. in the liquid phase a benzene compound with argentic fluoride in the range of from about 0.1 mol to about 1 mol per mol of said benzene compound, said compound being dissolved in an inert solvent therefor present in amounts ranging from about 99% to 50% solvent and the remainder being said benzene compound for a time sufficient to convert said argentic fluoride to argentous fluoride, and recovering said fluorinated benzene compound in good yield and purity.

2. The process according to claim 1 wherein the reaction is carried out under reflux temperatures.

3. The process according to claim 1 wherein the reaction is carried out in hexane.

4. The process according to claim 1 wherein the benzene compound is benzene.

* * * * *